US005195536A

United States Patent [19]
Silva et al.

[11] Patent Number: 5,195,536
[45] Date of Patent: Mar. 23, 1993

[54] SELF-ADHERING NONINVASIVE INTRACORPOREAL MOVEMENT DETECTOR

[75] Inventors: Fidel H. Silva, Sandy; Dwayne R. Westenskow; Joseph A. Orr, both of Salt Lake City, all of Utah

[73] Assignee: Axon Medical, Inc., Salt Lake City, Utah

[21] Appl. No.: 758,616

[22] Filed: Sep. 12, 1991

[51] Int. Cl.$^5$ .............................................. A61B 5/103
[52] U.S. Cl. ................................... 128/782; 128/775; 128/778
[58] Field of Search ............... 128/774, 778, 775, 782, 128/748, 721, 675, 687, 670; 73/700, 715, 730, 731

[56] References Cited

U.S. PATENT DOCUMENTS

| | | | |
|---|---|---|---|
| 3,913,563 | 10/1975 | Ball | 128/775 |
| 3,945,373 | 3/1976 | Tweed et al. | 128/782 |
| 4,122,837 | 10/1978 | Leonard | 128/774 |
| 4,421,124 | 12/1983 | Marshall | 128/782 |
| 4,576,181 | 5/1986 | Wallace et al. | 128/675 |
| 4,640,295 | 2/1987 | Isaacson | 128/748 |
| 4,989,615 | 2/1991 | Hochbert | 128/774 |
| 5,022,402 | 6/1991 | Schieberl et al. | 128/671 |
| 5,070,888 | 12/1991 | Hon et al. | 128/778 |

FOREIGN PATENT DOCUMENTS 203768 12/1985 Fed. Rep. of Germany .

OTHER PUBLICATIONS

Bell, Robin, "Measurement of spontaneous uterine activity in the antenatel patient", *Am. J. Obset. Gynecol.*, vol. 140, No. 6, 1981, pp. 713–715.

Corometrics advertisement, Medical Systems, Inc. (date unknown).
Graseby Respiration Sensor (photocopy of package & device), Aug. 1990.
LaCroix, George, "Monitoring labor by an external tokodynamometer", *American Journal Obstetrics and Gynecology*, May 1, 1968, pp. 111–119.
Parsely, Quentin, "The Act Disposable Tocotonometer", International Biomedics, Inc., Sep. 1988, pp. 1–3.
Smyth, C. N. "The Guard-Ring Tocodynamometer", *British Journal of Obstetrics and Gynecology* vol. 64 pp. 59–66, 1957.

Primary Examiner—Max Hindenburg
Assistant Examiner—Guy V. Tucker
Attorney, Agent, or Firm—Trask, Britt & Rossa

[57] ABSTRACT

A non-invasive intracorporeal movement transducer for translating intracorporeal movement into a detectable pressure signal is described. The movement transducer includes a fluid-filled bubble with a rigid rear portion, and a semi-rigid, flexible forward portion which is placed against a patient's skin above the organ to be monitored. The rear portion of the bubble has a fluid duct which provides fluid communication to the interior, and tubing is connected between the duct and a pressure sensor which detects the pressure of fluid within the bubble. Self-adhering attachment means is associated with the rear portion of the bubble for affixing the bubble against the patient's skin. In one embodiment, the attachment means is a foam backing larger than the bubble, with adhesive on one side for adhering to the patient's skin and to the rear portion of the bubble. The backing holds the rigid rear plate substantially fixed in approximately parallel relation to the patient's skin surrounding the area covered by the bubble.

17 Claims, 6 Drawing Sheets

SELF-ADHERING NONINVASIVE INTRACORPOREAL MOVEMENT DETECTOR

BACKGROUND OF THE INVENTION

1. Field

The application relates to monitoring of internal organs, and more particularly to noninvasive detection of intracorporeal movement and pressure.

2. State of the Art

Intra-corporeal movement can be detected as changes in pressure of a pressure-sensitive detector mounted on the patient's skin over the organ to be monitored. One area in which such methods have been applied is that of preterm monitoring of uterine contractile activity in pregnant women. Uterine activity may be an important predictor of preterm labor (premature delivery) (R. Bell, Brit. J. Obstet. and Gyn. 90:884–887, 1983; Wood et al, Am. J. Obst. & Gynec. 91:396–402, 1965). Measurement of intrauterine pressure is also important for the diagnosis and treatment of difficult labor due to unusually large fetus, abnormal position of fetus, obstructed birth canal, or other factors (Smyth, Brit. J. Obstet. and Gyn. 64:59–66, 1957). A device for measuring intrauterine pressure is sometimes referred to as a tocotonometer or tocodynamometer.

A device for intrauterine pressure monitoring should be noninvasive, reliable, and sensitive to the pressure sought to be measured. It is especially desirable for such a device to be simple enough for a patient to use unassisted at home and comfortable enough to wear for extended periods, while still providing accurate results. It is further desirable that the device not be overly sensitive to motions of the patient which do not relate to uterine contraction.

Many prior intrauterine pressure monitoring devices require a belt which straps the pressure detecting device to the patient's abdomen. For example, devices described by Smyth (ibid) and in U.S. Pat. No. 3,945,373 to Tweed et al each have a flat guard ring with a plunger-like sensor disposed in the central opening of the ring. The guard ring must be pressed firmly against the abdomen by a belt or strap. The plunger is spring mounted and the displacement of the plunger relative to the guard ring reflects the pressure in the abdomen. Plunger displacement may be measured by a variety of types of displacement sensors.

Tocotonometers of this type have a number of disadvantages. For example, accuracy of the measurements depends upon proper placement of the transducer and upon belt tension. Respiratory movements are translated by the belt into pressure compressing the tocotonometer transducer and producing signals unrelated to abdominal contraction. Measurements are quantitative only with regard to the frequency and duration of the contraction, because the signal from the displacement sensor does not quantitatively reflect the strength of the contraction. Moreover, such devices are useless with obese patients.

Additionally, these devices are too uncomfortable for extended wear by many patients, and may shift due to patient movement thereby producing less accurate readings. The patient's movements are severely restricted, because the transducer must be removed in order for the patient to move any significant distance away from the attached monitor. When the transducer is removed and then replaced on the abdomen, the positioning of the transducer and tension with which it is attached are critical to obtaining repeatable and interpretable results, and must be performed by trained personnel. Even then the results are subject to variation.

Recently, Corometrics Medical Systems, Inc. of Wallingford, Conn. has introduced a guard ring tocotonometer which is purportedly maintained in position on the patient's abdomen with an adhesive baseplate. However, only the cover baseplate is disposable, not the sensor. Moreover, the discomfort occasioned by the plunger-type sensor is not alleviated. Finally, if the patient is to be moved from the vicinity of the monitor, the sensor must be removed and later replaced and readjusted to obtain proper readings.

Another type of device, described in U.S. Pat. No. 4,989,615 to Hochberg, has a soft, fluid-filled bladder element which may be pressurized or internally-supported, depending upon the embodiment. A pressure monitor is disposed to detect changes in pressure in the fluid within the bladder due to the hardening of the abdomen during uterine contractions. This device also requires a belt or body stocking to hold the bladder with some pressure against the patient's abdomen, and is subject to problems similar to those outlined in regard to the guard ring tocotonometers of Smyth and Tweed et al.

Accordingly, a need remains for a non-invasive intracorporeal movement detector which is attached to a pregnant patient's abdomen without a belt and which overcomes the above-enumerated disadvantages of previous tocotonometers.

SUMMARY OF THE INVENTION

The invention is a non-invasive intra-corporeal movement transducer for translating intra-corporeal movement into a detectable pressure signal. The movement transducer includes a bubble which is hollow and has a rigid rear portion, a semi-rigid forward portion for placement against a patient's abdomen, and an interior filled with fluid. A pressure sensor is disposed to sense the pressure of fluid within the bubble. Self-adhering attachment means is associated with the rear portion of the bubble for affixing the bubble against a skin surface of a patient's abdomen. The attachment means is constructed to hold the rigid rear portion in substantially fixed relation to the skin surface.

In a preferred embodiment, the rear portion of the bubble has a fluid duct which provides fluid communication to the interior, and a tube is connected between the duct and the pressure sensor. Desirably, the tube has a relatively narrow inner diameter. This is believed to help filter out rapid pressure changes of relatively small magnitude, such as those caused by respiration or shivering. Also, use of narrow tubing reduces dead volume in the system so that changes in the abdominal pressure produce a larger signal.

In a preferred embodiment, the rigid rear portion comprises a rear bubble wall which is semi-rigid and integral with said forward portion and a rigid plate externally adapted to the rear wall. The rigid plate is sized and positioned to at least cover the rear wall. The bubble walls including both the forward portion and the rear wall are desirably formed of highly plasticized polyvinyl, silicone, hard rubber, or the like. The precise desirable thickness of the walls is selected to provide an appropriate deformation of the bubble in response to a force in the range of 1 kilogram applied to the bubble.

Preferably, the bubble walls are relatively thick and for polyvinyl, should be between about 0.06" and 0.12".

In one embodiment, the attachment means is a foam backing larger than the bubble, with adhesive on one side for adhering to the patient's skin and to the rear portion of the bubble. The backing is constructed and positioned to hold the rigid rear plate substantially fixed in approximately parallel relation to the patient's skin surrounding the area covered by the bubble.

When the plate is held in such fixed relation to the patient's surrounding skin, it ensures that upward movements from within the patient's body toward the skin (such as uterine contractions) cause a change in pressure within the bubble, instead of simply a deflection of the whole bubble, or a bulge elsewhere in the bubble without a change in its interior pressure.

DETAILED DESCRIPTION OF THE ILLUSTRATED EMBODIMENT

Figure 1:
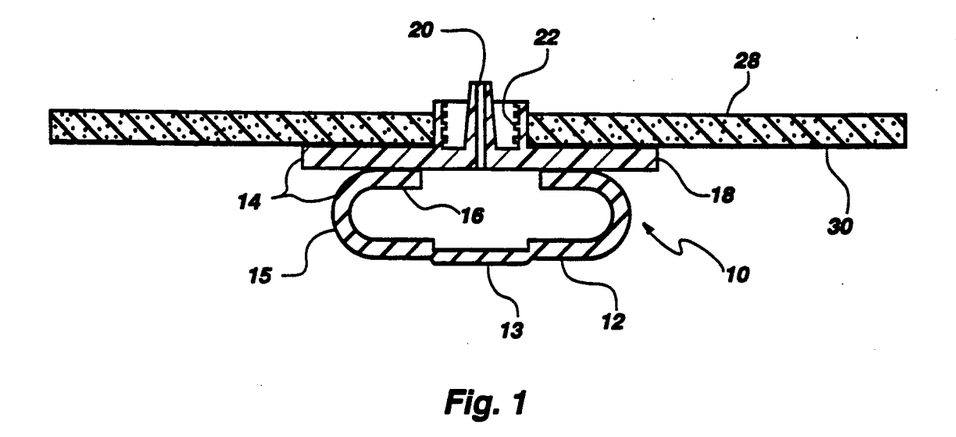
FIG. 1 is a side plan view of a bubble transducer of the invention.

In FIG. 1, a substantially circular bubble generally indicated at 10 has a forward portion 12 and a rear portion 14 in brackets. Rear portion 14 includes annular rear wall 16, which is integral with forward portion 12 (also referred to hereinafter as forward wall 12) and extends thereinto at the lateral periphery 15 of bubble 10. A circular rigid plate 18 is centered over and sealingly secured to rear wall 16. Forward portion 12 is for placement proximate to the patient's skin on the body part within which it is desired to detect inner movement, for example the abdomen of a pregnant woman.

Forward and rear walls 12, 16 in conjunction with plate 18 define a closed interior volume of bubble 10. This volume is filled with a fluid. While almost any fluid could be used to fill bubble 10, for convenience a preferred embodiment uses air at about atmospheric pressure. Changes in the interior volume, caused for example by pressure exerted on the forward wall portion 12 by uterine contractions, will cause a change in fluid pressure within the bubble.

In the illustrated embodiment, there is a gap between the inner edges of wall 16, which is spanned by plate 18 to complete the enclosure of bubble 10. However, wall 16 could also be formed without a gap except for duct 20, and the arrangement of plate 18 would be unaffected by such a change. Back plate 18 may be made of any substantially rigid material, but preferably is lightweight and inexpensive, such as a polycarbonate or hard polyethylene plastic.

Wall portions 12, 14 are formed of a semi-rigid or stiffly flexible material similar to hard rubber, so that the abdominal wall against which it is placed will be indented slightly, and without appreciable compression of the bubble. Desirably, there should be a substantially linear relationship between the force exerted on front wall portion 12 (for example by uterine contractions) and fluid pressure within the bubble interior. To achieve such a relationship, it has been found that the material and the thickness of the walls is important. If the walls are too thin and/or too flexible, when pressure is exerted on the forward wall the rear walls may tend to bulge so that there is little change in interior volume of the bubble. At present, satisfactory results appear to be obtained with a highly plasticized polyvinyl PLASTISOL of thickness between about 0.06" and 0.12", manufactured by Dempsey Industries of Miamisburg, Ohio (catalog no. DB240). In a preferred embodiment, walls made of PLASTISOL are from about 0.06" to about 0.08" in thickness. Dempsey Industries certifies that PLASTISOL has the following typical properties: hardness (ASTM D-2240), instantaneous 68, at 15 seconds 61; tensile strength (ASTM D-412 Die C), 1750 psi; elongation (ASTM D-412 Die C), 380%; tear strength (ASTM D-1004), 220 pli; specific gravity (ASTM D-792, Method A-1), 1.19; weight per gallon, 9.82; solids content, 99% minimum.

Other materials such as hard rubber, silicone, polyurethane, etc., are also suitable, though the precise optimal wall thickness may be different than with the PLASTISOL polyvinyl described above. As a semi-objective measure, it appears that a bubble which has small to moderate deformation when about 1 kilogram of force is applied is desirable, and it is recommended practice when utilizing the transducer of the present invention to reference calibrae a bubble for chart reading purposes by application of 1 kilogram of force. Preferably also, the changes in internal pressure of the bubble should be approximately linear with force in the range of 1 kg (see for example FIG. 7).

It will be noted that the bubble 10 of the present invention as depicted in FIG. 1 includes a circular discontinuity or button 13 in forward wall portion 12. While such a feature is not necessarily required for operation of the movement transducer of the invention, it is believed to provide desirable rigidity to the center of forward wall portion so that flexing of the bubble 10 response to intracorporeal movement will primarily be in the vicinity of lateral periphery 10 and substantially uniform therearound. Button 13 may take other forms, such as a nipple-shaped protrusion, or may extend radially farther than is shown in FIG. 1, such design modification being dependent upon the material selected for the bubble and the wall thickness thereof. Use of a button 13 in forward portion 12 appears to provide greater transducer sensitivity to intracorporeal movement without rendering the system susceptible to background respiratory, or other patient movement.

Figure 2:
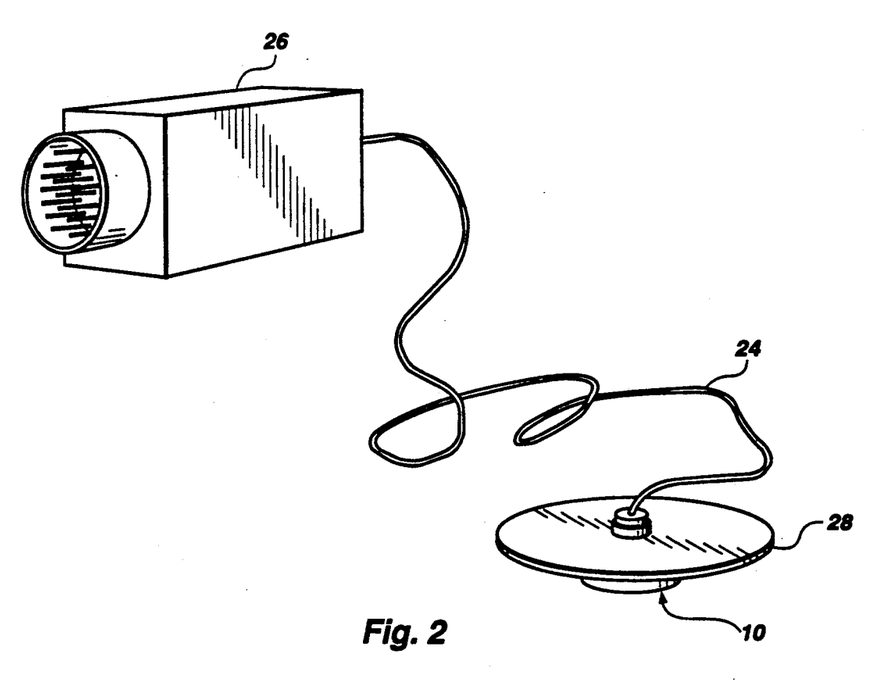
FIG. 2 is a perspective view of the bubble transducer with associated elements.

Fluid communication between the interior of bubble 10 and an external pressure sensor is provided by duct means here shown as a duct 20 extending through the center of plate 18 and having associated therewith a Luer-lock type fitting 22 preferably integral with plate 18. It is not required that fitting 22 be of the type permitting connection and disconnection therefrom, but it is highly desirable as it allows the patient to move from bed by disconnecting tubing 24 while leaving bubble 10 in place. Fitting 22 constitutes tubing connection means for connecting duct 20 to a length of tubing 24 which communicates with a fluid pressure sensor disposed within interface box 26. Tubing 24 is preferably of a relatively narrow internal diameter so that resistance to fluid is substantial, and dead air space is minimized. Preferably also, tubing 24 is inelastic at the pressures to be measured, and not too flexible. Good results are obtained with a non-kinking polyvinylchloride tubing of inner diameter about 0.03" and an outer diameter of about 0.08". It is further desirable that tubing 24 be colored rather than clear, so that it may be more readily distinguished from other medical tubing.

Interface box 26 is in turn detachably electrically connectable to an electronic monitor (not shown) known in the art to provide pressure signals reflective of the pressure within bubble 10. Such monitoring electronics may include signal processing circuits and a chart recorder, as known in the art. Interface box 26, an exemplary embodiment of which will be described in greater detail hereinafter, may preferably be constructed to interface with monitoring electronics in commercial use with prior art pressure monitors.

A circular backing 28 which constitutes self-adhering attachment means is placed over the rear side of plate 18 substantially concentrically therewith to surround duct 20 and fitting 22, and extends substantially beyond the edges of plate 18 in all directions. Backing 28 has an adhesive side 30 of a substance which adheres to the patient's skin and to plate 18 tightly enough to prevent shifting of the plate and bubble 10. The size of backing 28 is selected to provide good adhesion and holding of bubble 10 against the patient's skin. In an exemplary embodiment having a bubble diameter of about 1.2" and a plate of diameter about 1.4", a backing of about 5" diameter was found to be adequate in conjunction with an acrylic skin adhesive.

Backing 28 should be made of a material with some flexibility, but not so soft as to permit bulging of the backing and displacement of the bubble upon strong application of force. It is believed that the optimum location for the bubble is on the patient's abdomen over the belly button, and adhesive 30 or backing 28 maintains the bubble against the skin of the patient with sufficient force to indent the abdominal wall and slightly compress bubble 10. A suitable material for backing 28 is a polyethylene foam ⅛" thick and of density about 4 lbs. per cubic foot. Such a material is available from Adchem Incorporated, New York, precoated on one side with a single coat of acrylic adhesive. A less dense foam, 2 lbs per cubic foot, has been found to allow too much bulging.

Alternatively, backing 28 may be eliminated and a hydrogel film may be used as an adhesive. In this embodiment, best results are obtained by adding a mylar stiffener of about 3 mils thickness over the hydrogel film in place of backing 28 to support the hydrogel and prevent sliding. An advantage of this embodiment is that the area of the patient's skin which is covered by the attachment means may be smaller than where an adhesive coated foam is employed and sweating beneath the device is less, providing greater patient comfort and better adhesion of the bubble. In addition, the hydrogel film may be removed from the patient's skin and reattached thereto a number of times without loss of adhesive properties.

Figure 6A:
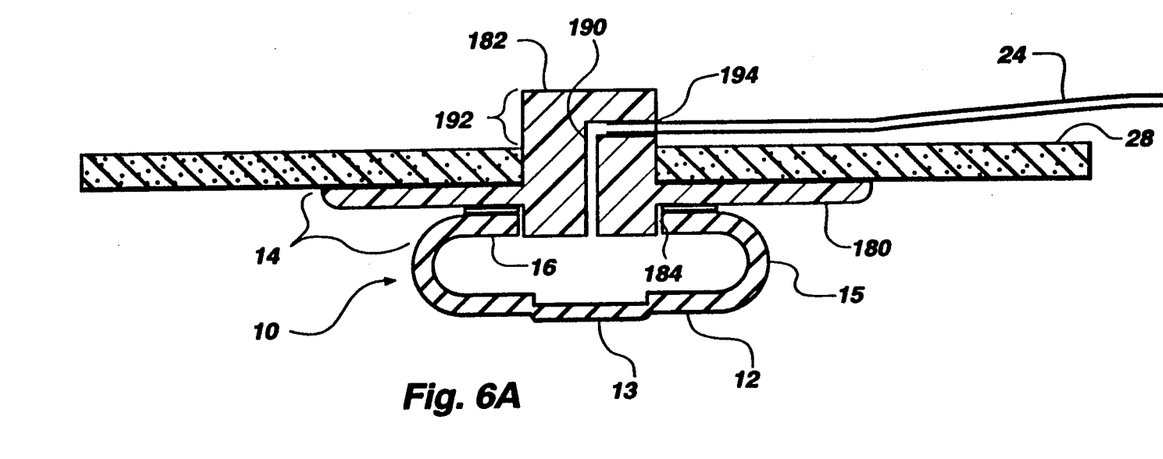
FIGS. 6A and 6B are a side plan view and a perspective view, respectively, of an alternate embodiment of a bubble transducer.
Figure 6B:
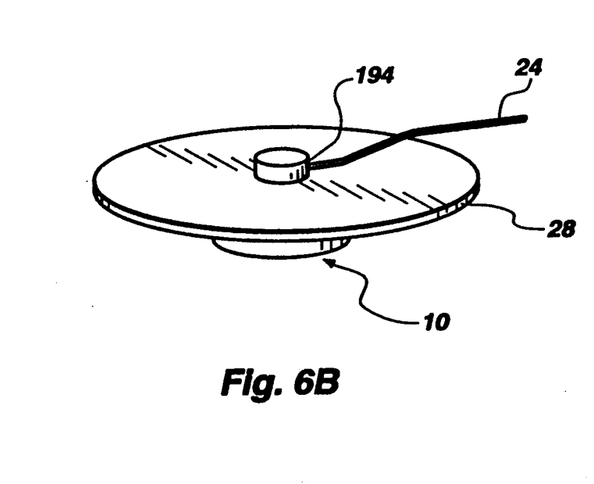

An alternate embodiment of the transducer illustrated in FIGS. 6A and 6B differs from that of FIGS. 1 and 2 primarily in the structure of the rear plate and associated duct. As seen in FIG. 6A, in the alternate embodiment a plate 180 is formed with a central cylindrical portion 182 which has an inner segment 184 fitting snugly within the gap in the rear wall 16 of the bubble. Plate 180 is sealingly secured to rear wall 16. An angled duct 190 is formed within an outer segment 192 of cylindrical portion 182. Duct 190 is connected to tubing 24 through an opening 194 in the side of cylindrical portion 182. Tubing 24 is sealingly seated within opening 194 and extends from it in a direction approximately parallel to rear wall 16, as is seen in FIGS. 6A and 6B. This is in contrast to the embodiment of FIGS. 1 and 2, in which tubing 24 extends from duct 20 in an initial direction approximately perpendicular to rear wall 16.

Figure 7:
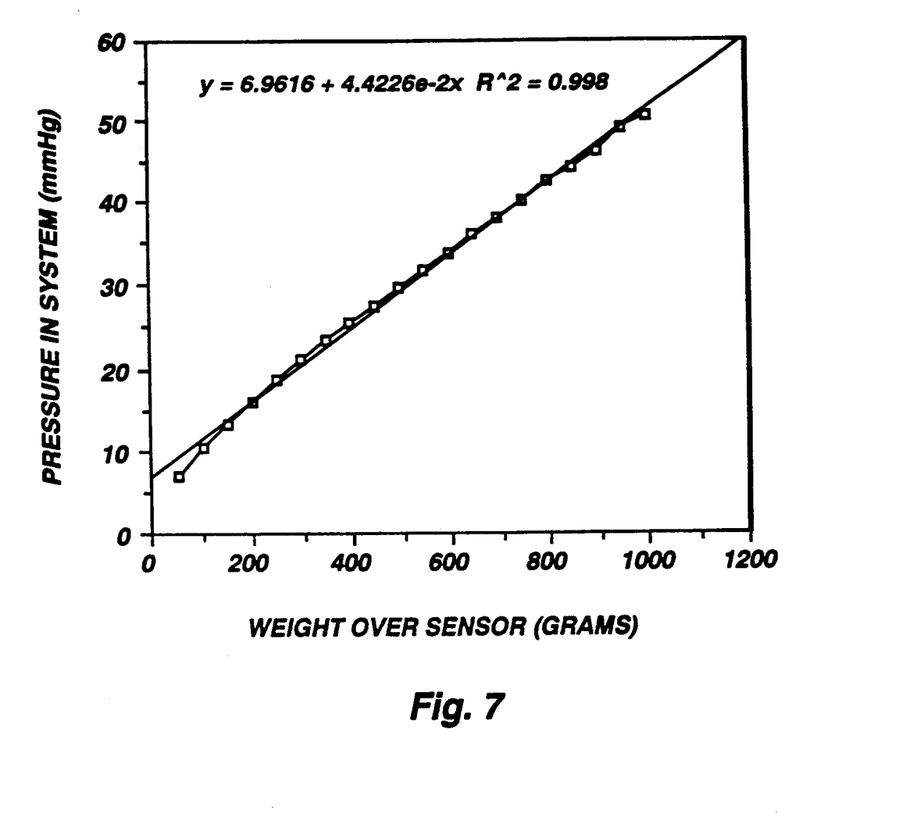
FIG. 7 is a chart illustrating the relationship between the air pressure in the transducer system and weight placed on the transducer.

FIG. 7 illustrates the defined response relationship between the internal system pressure and external weight placed on the bubble in a working embodiment of the bubble transducer of the present invention.

Figure 3:
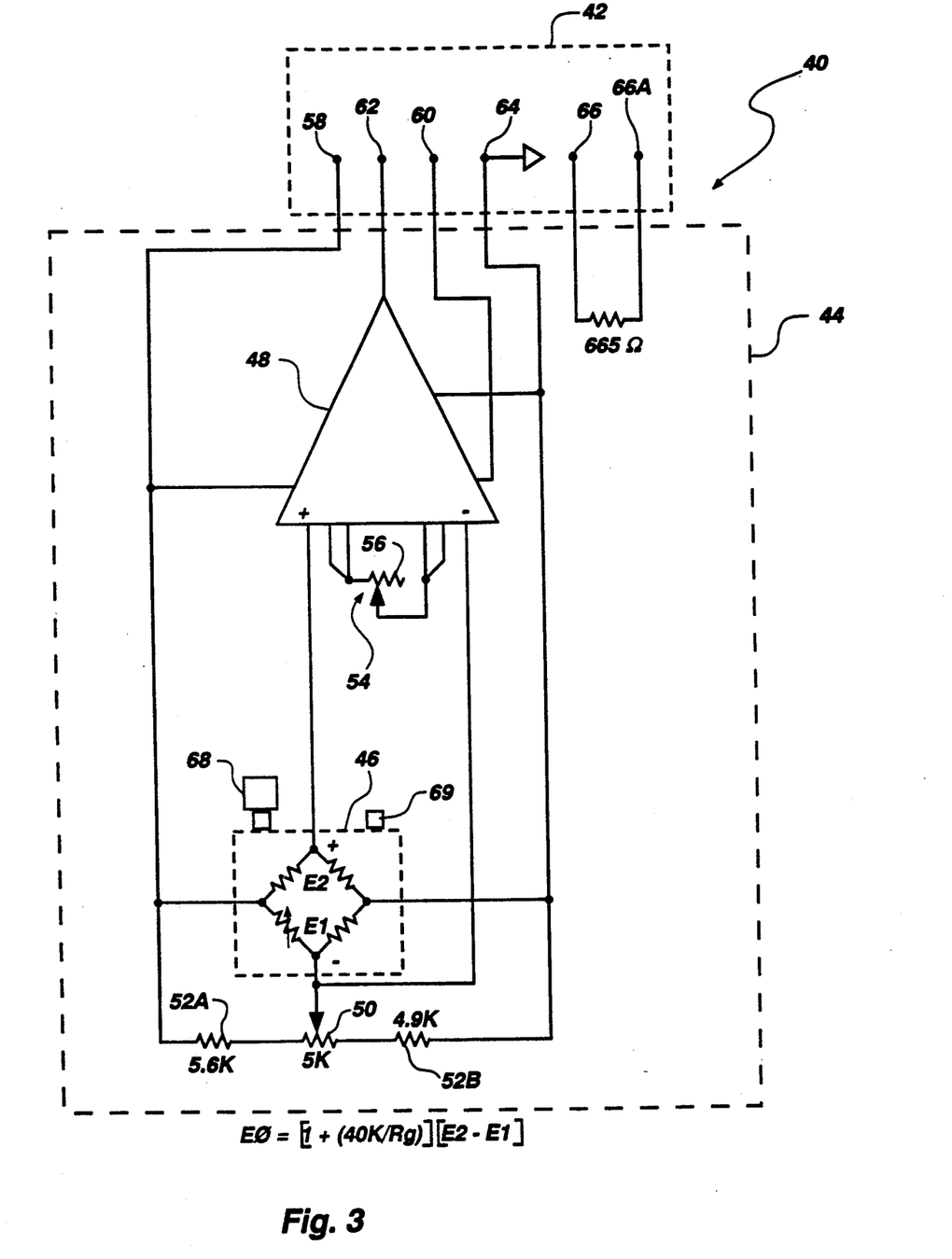
FIG. 3 is a schematic illustrating the components of an interface box for use with the bubble transducer.

FIG. 3 is a schematic diagram of the components of an exemplary embodiment of an interface box 26 useful with the bubble transducer. The interface box 26 of FIG. 3 can be directly connected to the monitoring electronics of a commercially available tocotonometer, the Hewlett-Packard model 15248A Toco Transducer. Interface box 26 includes a toco connector 42 which is configured as a Hewlett-Packard 8040A and a housing 44 in which a pressure sensor 46 and an amplifier 48, here chosen to be a Burr-Brown instrumentation amplifier 1NA101, are disposed. Pressure sensor 46 and amplifier 48 are electrically connected to input leads on connector 42. Tubing connector 68 connects the output end tubing 24 of the movement transducer of the present invention to pressure sensor 46. Pressure port 69 provides an atmospheric reference pressure for sensor 46.

Pressure sensor 46 may be a commercially available resistance-bridge type pressure sensor such as the SX01DN made by SenSyn, including a zero adjust embodied as a potentiometer 50. Sensor 46 is preferably temperature-compensated and provides a substantially linear response to pressure over the range of about 1 psi with the midpoint of the range being around 0.5 psi above atmospheric pressure. The values of resistors 52A, 52B are selected as known in the art to provide appropriate signal levels to the monitor electronics via connector 42. Values selected for a working embodiment are indicated in kilo-ohms in FIG. 3. Amplifier 48 has an associated adjustable gain indicated generally at 54 and here chosen to be a 5K Ω potentiometer with resistor 56 selected to provide the desired signal output strength. Connector 42 provides connections 58, 60 respectively to twelve volt positive and negative voltages from the monitoring electronics as needed for operation of sensor 46 and amplifier 48. A signal output connection 62, a ground connection 64, and mode resistor connections 66, 66A are also provided by connector 42. All of these connections are adapted to connect to the appropriate inputs/outputs on the aforementioned available Hewlett Packard toco monitoring device (not shown), and may also be adapted for use with other commercially available units. The voltage equation for the output voltage $E\phi$ from the interface box 26 of the illustrated embodiment is shown at the bottom of FIG. 3.

In a preferred embodiment, both a high gain and a low gain for the incoming signal are provided. Because of the improved signal-to-noise ratio provided by the bubble transducer system, the provision of a high gain makes it possible to accurately and reliably detect contractions of lower intensity than is possible with typical prior toco transducers.

Figure 4:
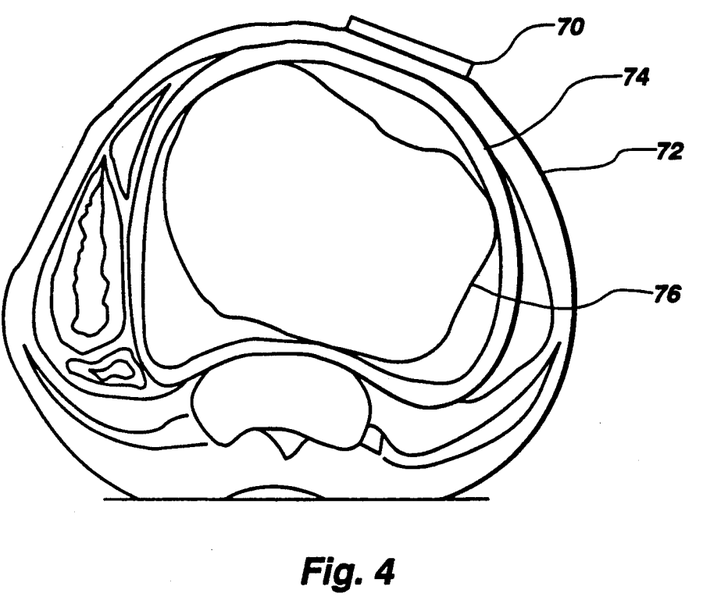
FIG. 4 is a diagram illustrating the placement for use as a tocotonometer of the bubble transducer of FIG. 1 and a prior art tocotonometer.

FIG. 4 is a stylized diagram showing a transducer 70 as it would be placed on the abdomen 72 above the uterus 74 of a pregnant woman. A fetus 76 is also indicated.

Figure 5A:
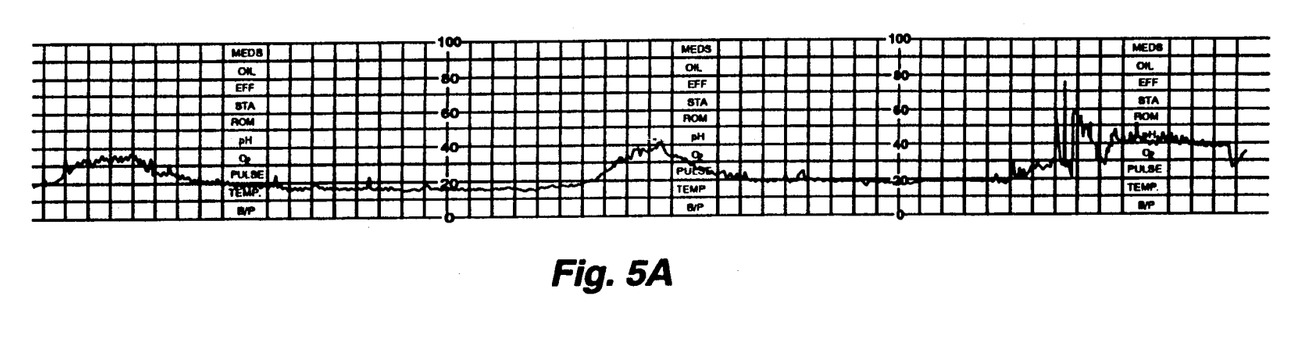
FIGS. 5A and 5B are charts of pressure readings obtained with a prior art tocotonometer and with the bubble transducer of the invention, respectively.
Figure 5B:
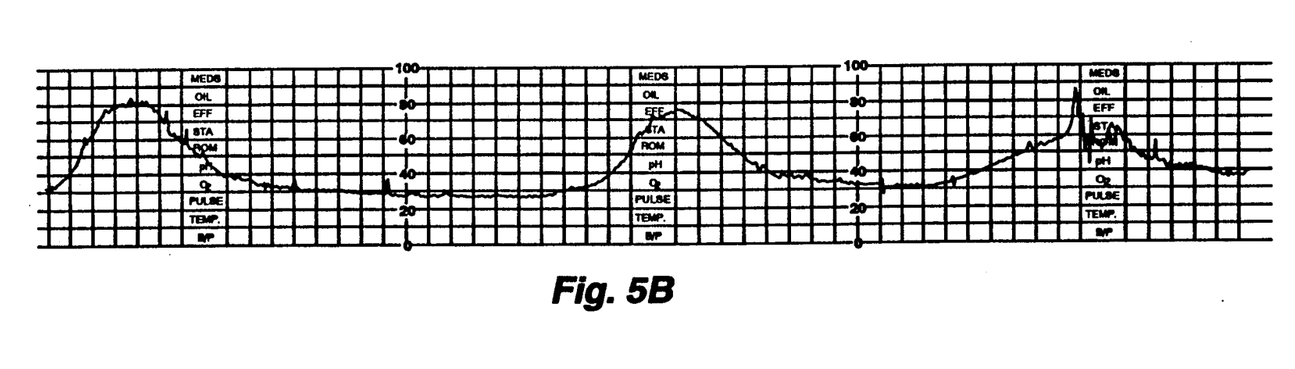

FIGS. 5A and 5B respectively are recordings made with a Hewlett-Packard Toco Transducer, and with a bubble transducer of the present invention, placed adjacent each other on the abdomen of the same pregnant woman. The Hewlett-Packard Toco Transducer is a commercially available transducer of the guard ring-type described previously herein. The Hewlett-Packard transducer was affixed by means of an elastic belt encircling the patient's torso and over the abdomen, whereas the invented bubble transducer was affixed by means of adhesive backing 28. It can be readily seen that the bubble transducer provides a significantly improved signal-to-noise ratio in comparison to the Hewlett-Packard transducer.

A significant advantage of the bubble transducer of the invention is that it is much more comfortable for the patient. Furthermore, the patient is at much greater liberty to move about, because tubing 24 can be easily detached from the associated electronic monitor without disturbing the placement of the transducer. The bubble itself is easily and inexpensively constructed by dip-molding of the plastic. Because it is inexpensive, the bubble can be disposable to avoid problems with contamination. Also, the electronic portion of the device are isolated from the patient, reducing or eliminating any electrical hazard.

While the invention is described with reference to specific embodiments, it will be recognized that various substitutions and alterations may be made without departing from the scope of the invention. For example, the bubble may be formed with a greater depth for use with obese patients; the tubing connections may be of another type; a pressure sensor might be incorporated in the transducer rather than in the interface box to reduce system air volume, although this is not preferred or required for effective operation of the invention. The claims themselves set forth the subject matter which the inventors regard as the invention.

What is claimed is:

1. A noninvasive intracorporeal movement transducer to use with an external monitor, comprising:
   a bubble defining a closed interior volume and including spaced laterally co-extensive front and rear walls resiliently joined at their periphery;
   a duct extending from said closed interior volume to the exterior of said bubble;
   tubing having one end thereof in communication with said duct via tubing connection means associated therewith;
   substantially planar attachment means affixed on one side to said bubble adjacent said rear wall, extending laterally therebeyond, and including an adhesive on the side thereof adjacent said bubble for securing said bubble to the skin of a patient with said forward wall of said bubble in contact with said skin; and
   a rigid back plate disposed between said rear wall and said attachment means, said back plate sized and positioned to overlay substantially the entire cross-sectional area of said bubble.

2. The movement transducer of claim 1, wherein said attachment means comprises a backing of area significantly greater than the cross-sectional area of said back plate, said backing having a first adhesive side disposed over said back plate and said bubble for contacting said skin of said patient's abdomen, a second side facing away from said patient's abdomen, and an opening sized and positioned for extension therethrough of said tubing connection means.

3. The movement transducer of claim 2, wherein said duct extends through said back plate and said tubing connection means is associated with said back plate.

4. The movement transducer of claim 2, wherein said back plate is held by said attachment means over said bubble in substantially fixed relation to said patient's skin.

5. The movement transducer of claim 2, further including a pressure sensor connected to the end of said tubing opposite that in communication with said duct for sensing changes in air pressure within said bubble transmitted through said tubing.

6. The movement transducer of claim 5, further including interface circuit means operably associated with said pressure sensor for providing electrical output signals proportional to said pressure changes to said external monitor.

7. The movement transducer of claim 1, wherein said front wall includes a rigid center region.

8. A noninvasive intracorporeal movement transducer, comprising:
   a hollow bubble defining a closed interior volume filled with fluid and including a stiff but flexible forward portion for disposition against the abdomen of a patient and a rigid rear portion including a rear bubble wall resiliently, peripherally joined to said forward portion, said bubble being constructed to have a substantially linear relationship between force exerted against an outer surface of said forward portion and pressure of said fluid within said closed interior volume, said forward portion and said rear bubble wall being formed of a material selected from the group consisting of polyvinyl, silicone and hard rubber and, having a thickness between about 0.06" and 0.12";
   a pressure sensor in communication with said closed interior volume for sensing pressure therein; and
   substantially planar attachment means overlying said bubble adjacent said rear portion thereof, extending peripherally therebeyond and including an adhesive on the side thereof adjacent said bubble for securing said bubble to said abdomen of said patient with said forward portion in contact therewith.

9. The movement transducer of claim 8, wherein said rear bubble wall is integral with said forward portion and said rigid rear portion further includes a rigid plate secured to said rear bubble wall.

10. A noninvasive intracorporeal movement transducer, comprising:
    a hollow bubble defining a closed interior volume filled with fluid and including a stiff but flexible forward portion for disposition against the abdomen of a patient and a rigid rear portion resiliently, peripherally joined to said forward portion;
    a pressure sensor in communication with said closed interior volume for sensing pressure therein;
    substantially planar attachment means overlying said bubble adjacent said rear portion thereof, extending peripherally therebeyond and including an adhesive on the side thereof adjacent said bubble for securing said bubble to said abdomen of said patient with said forward portion in contact therewith;

a duct associated with said rigid rear portion providing fluid communication to said closed interior volume; and a tube extending between said duct and said pressure sensor.

11. The movement transducer of claim 10, wherein said tube has an interior diameter of between about 0.02" and 0.04", and walls of a thickness similar to said interior diameter.

12. A noninvasive intracorporeal movement transducer, comprising:

bubble transduction means placeable against a skin surface of a patient's abdomen for translating force exerted from within said patient's abdomen toward said skin surface into a detectable pressure signal, comprising a hollow bubble having
a rigid rear portion,
a forward portion for placement against said skin surface, said forward portion including a substantially rigid center region and being joined to said rear portion at a flexible periphery,
an interior filled with fluid, and
a duct associated with said rear portion for providing fluid communication to said interior;

a pressure sensor disposed to sense the pressure of said fluid through said duct; and self-adhering attachment means associated with said rear portion of said bubble for affixing said bubble means to said skin surface with said rear portion held over said forward portion in substantially fixed relation to said skin surface.

13. The movement transducer of claim 12, wherein said attachment means comprises a backing of area significantly greater than the cross-sectional area of said rigid rear portion of said bubble, said backing having an adhesive side disposed over said rear portion with adhesive means disposed on said adhesive side for adhering said backing to said rear portion and said patient's skin.

14. The movement transducer of claim 13, wherein said rigid rear portion comprises a rear bubble wall which is integral with said forward portion and a rigid plate affixed to and over said rear bubble wall.

15. The movement transducer of claim 14, wherein said forward portion and said rear bubble wall are formed of a material selected from the group consisting of: polyvinyl, silicone, and hard rubber; and having a thickness between about 0.06" and 0.10".

16. The movement transducer of claim 12, further including a tube connected between said duct and said pressure sensor.

17. A noninvasive intracorporeal movement transducer, comprising:

a bubble defining a closed interior volume filled with fluid and including spaced laterally co-extensive front and rear walls joined at their periphery;

a pressure sensor in communication with said closed interior volume for sensing pressure therein;

substantially planar attachment means affixed on one side to said bubble adjacent said rear wall, extending laterally therebeyond, and including an adhesive on the side thereof adjacent said bubble for securing said bubble to the skin of a patient with said forward wall of said bubble in contact with said skin; and a rigid back plate disposed between said rear wall and said attachment means, said back plate sized and positioned to overlay substantially the entire cross-sectional area of said bubble.

* * * * *